United States Patent
Bernard et al.

(10) Patent No.: US 10,358,657 B2
(45) Date of Patent: Jul. 23, 2019

(54) **IS-TARGETING SYSTEM FOR GENE INSERTION AND GENETIC ENGINEERING IN *DEINOCOCCUS* BACTERIA**

(71) Applicant: DEINOVE, Grabels (FR)

(72) Inventors: Rémi Bernard, Castelnau le Lez (FR);
Esther Gerber, Saint Drezery (FR);
Elena Hauser, Grabels (FR);
Jean-Paul Leonetti, Castelnau le Lez (FR)

(73) Assignee: DEINOVE, Grabels (FR)

( * ) Notice: Subject to any disclaimer, the term of this patent is extended or adjusted under 35 U.S.C. 154(b) by 0 days.

(21) Appl. No.: 15/039,867

(22) PCT Filed: Dec. 19, 2014

(86) PCT No.: PCT/EP2014/078858
§ 371 (c)(1),
(2) Date: May 27, 2016

(87) PCT Pub. No.: WO2015/092013
PCT Pub. Date: Jun. 25, 2015

(65) Prior Publication Data
US 2016/0376609 A1 Dec. 29, 2016

(30) Foreign Application Priority Data
Dec. 20, 2013 (EP) .................... 13306811

(51) Int. Cl.
*C12N 15/90* (2006.01)
*C12N 1/20* (2006.01)
*C12N 15/74* (2006.01)
*C12P 21/00* (2006.01)

(52) U.S. Cl.
CPC ............ *C12N 15/902* (2013.01); *C12N 1/20* (2013.01); *C12N 15/74* (2013.01); *C12P 21/00* (2013.01); *C12N 2800/90* (2013.01)

(58) Field of Classification Search
None
See application file for complete search history.

(56) References Cited

FOREIGN PATENT DOCUMENTS

| EP | 2 251 415 | 11/2010 |
| WO | WO 02/14490 | 2/2002 |

OTHER PUBLICATIONS

Gray, Y. H. M. "It takes two transposons to tango: transposable-element-mediated chromosomal rearrangements" *Trends in Genetics*, Oct. 2000, pp. 461-468, vol. 16, No. 10.
Islam, M.S. et al. "Characterization and distribution of IS8301 in the radioresistant bacterium *Deinococcus radiodurans*" *Genes Genetic Systems*, 2003, pp. 319-327, vol. 78, No. 5.
Mahillon, J. et al. "IS elements as constituents of bacterial genomes" *Research in Microbiology*, Jan. 1, 1999, pp. 675-687, vol. 150, No. 9/10.
Makarova, K.S. et al. "Short repeats and IS elements in the extremely radiation-resistant bacterium *Deinococcus radiodurans* and comparison to other bacterial species" *Research in Microbiology*, Nov. 1, 1999, pp. 711-724, vol. 150, No. 9/10.
Pasternak, C. et al. "ISDra2 transposition in *Deinococcus radiodurans* is downregulated by TnpB" *Molecular Microbiology*, Apr. 1, 2013, pp. 443-455, vol. 88, No. 2.
Written Opinion in International Application No. PCT/EP2014/078858, dated Mar. 13, 2015, pp. 1-5.

*Primary Examiner* — Nancy A Treptow
(74) *Attorney, Agent, or Firm* — Saliwanchik, Lloyd & Eisenschenk (57) ABSTRACT

The present invention relates to methods and compositions for chromosome integration of nucleic acids into *Deinococcus* bacteria. The invention more particularly relates to IS-mediated multicopy gene insertion or chromosome engineering in *Deinococcus* bacteria, the resulting bacteria, and the uses thereof.

12 Claims, 3 Drawing Sheets
Specification includes a Sequence Listing.

IS-TARGETING SYSTEM FOR GENE INSERTION AND GENETIC ENGINEERING IN *DEINOCOCCUS* BACTERIA

CROSS-REFERENCE TO RELATED APPLICATION

This application is the U.S. national stage application of International Patent Application No. PCT/EP2014/078858, filed Dec. 19, 2014.

The Sequence Listing for this application is labeled "Seq-List.txt" which was created on Jan. 23, 2015 and is 18 KB. The entire content of the sequence listing is incorporated herein by reference in its entirety.

The present invention relates to methods and compositions for chromosome integration of nucleic acids into *Deinococcus* bacteria. The invention more particularly relates to IS-mediated multicopy gene insertion or IS targeting methods for chromosome engineering in *Deinococcus* bacteria, the resulting bacteria, and the uses thereof.

INTRODUCTION

*Deinococcus* is a gram positive bacterium that was isolated in 1956 by Anderson and collaborators. This extremophile organism is resistant to DNA damage by UV and ionizing radiations or by cross-linking agent (mitomycin C) and is tolerant of desiccation. WO01/023526 shows the unusual resistance of *Deinococcus* to radiation and further proposes their engineering and use in bioremediation. WO2009/063079 shows that *Deinococcus* bacteria can resist solvents and transform biomass to generate biofuels. WO2010/130806 further discloses recombinant *Deinococcus* strains wherein ethanol biosynthesis genes have been inserted. These recombinant strains exhibit improved performance in the production of ethanol.

The present invention discloses novel compositions and methods for genetically modifying *Deinococcus* bacteria. More specifically, the invention provides improved Insertion Sequence-based methods for genetically modifying *Deinococcus* bacteria.

SUMMARY OF THE INVENTION

The invention relates to methods and constructs for gene recombination or chromosome engineering in *Deinococcus* bacteria. More specifically, the invention relates to IS-based methods and constructs for gene insertion or amplification in *Deinococcus* bacteria, or IS-mediated genetic modification of *Deinococcus* bacteria.

An object of the invention therefore relates to a method for introducing a nucleic acid into the genome of a *Deinococcus* bacterium, comprising introducing said nucleic acid into said genome by IS-mediated insertion. In preferred embodiments, the nucleic acid is introduced into the genome of the bacterium by homologous recombination with an IS present in the genome, by intron-mediated insertion into an IS, or by IS-mediated transposition.

A further object of the invention resides in a method for producing a recombinant *Deinococcus* bacterium comprising one or several copies of a gene of interest inserted into its genome, the method comprising introducing said gene of interest into the genome of said bacterium by IS-mediated insertion and, optionally, amplifying the copy number by subjecting said bacterium or a descendant thereof to a gene amplification treatment.

The invention also relates to a method for inducing (or increasing) chromosomal rearrangement(s) or shuffling in a *Deinococcus* bacterium, the method comprising expressing (or increasing expression of) at least a transposase gene in said bacterium.

The invention also relates to a *Deinococcus* bacterium obtained by IS-mediated insertion of a nucleic acid, or a descendant of said bacterium.

Another object of the invention is a *Deinococcus* bacterium comprising one or several copies of a nucleic acid inserted into an IS element.

A further object of the invention resides in a nucleic acid molecule comprising a gene of interest flanked, on one or both sides, by (i) a sequence homologous to a sequence of *Deinococcus* IS element or (ii) a sequence of an inverted repeat sequence of *Deinococcus* IS element.

The invention also relates to a recombinant *Deinococcus* bacterium comprising one or several copies of a transposase gene under control of a promoter.

The invention may be performed with any *Deinococcus* bacteria and can be used to engineer bacteria with improved genotypes or phenotypes, particularly bacteria which express recombinant genes of interest.

DETAILED DESCRIPTION OF THE INVENTION

The invention relates to IS-mediated gene insertion or chromosome engineering in *Deinococcus* bacteria, the resulting bacteria, and the uses thereof.

Insertion Sequences (IS) are transposable genetic elements identified in certain prokaryotic organisms. They have a typical length ranging from 300 to 3000 bp (Mahillon and Chandler, 1998; Chandler and Mahillon, 2002). In bacteria, IS are frequently found as part of natural plasmids. IS typically possess one or two open reading frames (ORFs) that encode a transposase, an enzyme that is necessary for their transposition. This (these) ORF(s) is (are) surrounded by linker regions that frequently end with short-terminal inverted repeats (IRs) ranging typically from 7 to 50 bp in length. Some IS may carry multiple repeated sequences at both ends, which may represent transposase binding sites (Zita Nagy and Michael Chandler, Research in Microbiology 155 (5) p 387-398). Contrary to transposons, IS do not contain ORF encoding drug resistance. Upon insertion, IS often undergo short directed repeats from 2 to 14 bp immediately outside the IRs.

Despite sequence divergence, IS have been grouped into families based on similarities and identities in the primary sequence of their transposases (Tpases) and in their genetic organization (Robinson, Lee, and Marx, 2012). This includes the disposition of their open reading frames (ORFs), the length and similarity of the terminal inverted repeats, and the characteristic number of base pairs in the target DNA which they duplicate upon insertion (Mahillon, Léonard, and Chandler, 1999).

Depending on the IS, insertion may be target site-selective (Craig, 1997; Tobes and Pareja, 2006). Through transposition, IS can interrupt the coding region of a gene, or disrupt promoter regions and alter gene expression. Given that there can be several copies of the same IS in a genome, IS can also serve as sites of DNA rearrangements such as deletions, duplications and inversions of adjacent DNA segments through homologous recombination (Robinson et al., 2012). Insertion sequences contribute to the variability of the prokaryotic genomes and phenotypes, and are thought to play an important role in the adaptability of prokaryotes to the environment (Schneider and Lenski, 2004).

IS elements have been identified in *D. radiodurans* (Makarova et al., 2001; Islam et al., 2003; Mennecier, Servant, Coste, Bailone, and Sommer, 2006; Pasternak et al., 2010). The present invention discloses the characterization of particular IS sequences in *Deinococcus* bacteria, as well as the uses thereof for genetic modification or shuffling of such bacteria.

More specifically, the inventors analyzed the presence and occurrence of different IS families in *Deinococcus* sp. genomes. A total of 11 IS families were found in 5 tested *Deinococcus* species, which are presented in Table 1. IS families IS4, IS5, IS1 and IS701 were found to be the most scattered among Deinococci, the largest family being IS4, which contains a total of 68 members in Deinococci. Surprisingly, the genomes of *D. geothermalis* DSM11300 and *D. geothermalis* MX6-1E possess a larger number of IS elements compared to the other *Deinococcus* strains (Table 1). In these strains, seventy six IS elements belonging to 10 distinct families were detected (DSM11300 strain) and fifty five spread into 7 IS families (MX6-1E strain).

The present invention therefore shows an unexpectedly high level number of insertion sequences in thermophile *Deinococcus* strains such as *D. geothermalis* (Table 1). This discovery brings new tools for genetic manipulation of thermophile *Deinococcus* strains and, in particular, allows multicopy integration of genes into *Deinococcus* bacteria to increase their expression. The presence of different IS families in a single *Deinococcus* genome even allows the introduction of different DNA constructs (one type of construct targets one family of IS). The present invention therefore provides a novel method to insert or spread or amplify a desired gene into a *Deinococcus* genome using *Deinococcus* insertion sequences.

The present invention also provides a method for chromosomal engineering of a *Deinococcus* bacterium by expressing or overproducing in said bacterium a transposase that targets an IS present (preferably in several copies) on the chromosome or a plasmid of said bacterium.

Definitions

Within the context of the present invention, the term "Insertion Sequence" or "IS" element designates a transposable genetic element comprising at least one transposase gene and a flanking terminal Inverted Repeat. IS are devoid of drug resistance gene. IS have a typical length ranging from 300 to 3000 bp, the terminal inverted repeats (IRs) ranging typically from 7 to 50 bp in length.

Preferred IS elements for use in the invention are *Deinococcus* IS elements, i.e., IS elements having the sequence of an IS present in one or, preferably, several copies in the genome of a *Deinococcus* bacterium. Specific examples of *Deinococcus* IS elements according to the invention are IS200/IS605; IS630; IS701; IS607; IS982; IS3; IS1; IS6; IS5; IS4; or IS66. The sequence of these IS is provided in the sequence listing.

"IS-based" methods or "IS-mediated" methods designates any method for inserting a gene in a *Deinococcus* bacterium which uses all or part of an IS element. Insertion is typically targeted, i.e., site-specific or site-controlled. In particular, because IS-mediated insertion generally follows target selectivity of the IS element, the gene insertion is not random but obeys the same rule.

The term "gene" designates any nucleic acid molecule (e.g., DNA fragment) of interest, such as preferably a nucleic acid comprising an ORF encoding a product (e.g., RNA or polypeptide) of interest. The gene may be natural, recombinant or synthetic. A gene may be single- or double-stranded, typically a DNA molecule. In a particular embodiment, the gene preferably encodes a protein, such as an enzyme. The gene may further comprise one or several regulatory elements operably linked to the ORF, such as a promoter, terminator, intron, etc.

The term "chromosomal engineering" designates any modification or rearrangement of a chromosome, such as a deletion, translocation, duplication, or inversion of one or several sequences within a chromosome or episome. Chromosomal engineering may result in novel chromosomes or episomes, thus creating novel biological pathways and/or genetic diversity in bacteria, leading to, e.g., bacteria having improved characteristics.

IS-Mediated Genetic Modification of a *Deinococcus*

As indicated the invention resides in IS-mediated genetic modification of *Deinococcus* bacteria, typically to produce recombinant or genetically improved bacteria. The invention is particularly advantageous since IS-mediated insertion is effective, can be site-selective, and allows insertion of multiple copies of a selected gene. IS-mediated insertion may comprise preferably the introduction of the gene into the genome of the bacterium by homologous recombination with a selected IS present (or inserted or amplified) in the genome of the bacterium; or by intron-mediated insertion into an IS present (or inserted or amplified) in the genome of the bacterium; or by IS-mediated transposition. The method may involve the use of an insertion cassette, the construction of artificial transposon, or the retro-homing mechanism of group II intron as described below, in combination or not with DNA-damaging treatments (UV, gamma, x-irradiation). Preferably, the IS-mediated insertion of a gene in a *Deinococcus* bacterium includes the (targeted) introduction of said gene into an IS sequence present in the genome of said bacterium.

The invention may be used to genetically modify any *Deinococcus* containing an IS element, preferably any *Deinococcus* strain that contains or that can accept at least two copies of an IS element. Examples of *Deinococcus* host strains that can be engineered according to the present invention include, without limitation, *D. geothermalis, D. radiodurans, D. cellulosilyticus, D. murrayi, D. guilhemensis, D. aerius, D. aerolatus, D. aerophilus, D. aetherius, D. alpinitundrae, D. altitudinis, D. apachensis, D. aquaticus, D. aquatilis, D. aquiradiocola, D. caeni, D. claudionis, D. daejeonensis, D. depolymerans, D. deserti, D. erythromyxa, D. ficus, D. frigens, D. gobiensis, D. grandis, D. hohokamensis, D. hopiensis, D. humi, D. indicus, D. maricopensis, D. marmoris, D. misasensis, D. mumbaiensis, D. navajonensis, D. papagonensis, D. peraridilitoris, D. pimensis, D. piscis, D. proteolyticus, D. radiodurans, D. radiomollis, D. radiophilus, D. radiopugnans, D. reticulitermitis, D. roseus, D. saxicola, D. sonorensis, D. wulumuqiensis, D. xibeiensis, D. xinjiangensis, D. yavapaiensis,* and *D. yunweiensis*. Preferred acceptor bacteria are thermophile *Deinococcus*. Most preferred bacteria are *Deinococcus* comprising at least 2 copies of an IS element, preferably at least 3 copies thereof. The copies may be present in the chromosome, or induced in said chromosome.

Accordingly, the method of the invention typically comprises the following steps:

a) provision of a *Deinococcus* bacterium that contains at least 1, preferably at least 2 copies of a target IS element; and, b) IS-mediated insertion of a gene into said target IS element.

Preferentially, the targeted IS is an IS present in more than one copy on the genome (chromosome and/or plasmid) of the selected *Deinococcus* bacterium. The targeted IS is more preferably one of the IS elements selected by the inventors which are listed in Table 1. The identification of several distinct IS elements, in addition, allows the propagation and expression of different genes of interest in a *Deinococcus* genome. A preferred target IS is selected from IS200/IS605; IS630; IS701; IS607; IS982; IS3; IS1; IS6; IS5; IS4; or IS66.

The *Deinococcus* bacterium may contain said at least 2 copies naturally, or may be treated to amplify the copy number of a target IS element, prior to step b), or thereafter. Accordingly, the invention generally comprises the following steps:

a) provision of a *Deinococcus* bacterium for which genetic modification is desired;

b) selection, in said *Deinococcus* bacterium, of at least one target IS element present in the chromosome of said bacterium, preferably in at least two copies;

c) optionally treating the bacterium to amplify the copy number of said selected target IS element; and d) inserting a gene into said bacterium by IS-mediated insertion into said selected target IS element.

In a particular embodiment, the step of treating the bacterium to amplify the copy number of the selected target IS element is conducted after the insertion step. Also, the amplification step can be performed both before and after the insertion step. The treatment may comprise any treatment which allows or increases expression or activity of a transposase and/or causes a cell stress, such as a thermal shock or an irradiation of the cells, which may be selected from UV, gamma and/or X ray irradiation, either alone or in combinations, most preferably UV irradiation(s). Irradiation treatment typically comprises subjecting the microorganisms to one or several sequential irradiations (e.g., from 1 to 5), which may be of the same or different nature, preferably of the same nature. Repeated irradiation treatments are typically carried out at intervals of between 1 and 8 hours, preferably 3 to 5 hours, and more preferably of about 4 hours. A particularly preferred treatment comprises subjecting the sample to UV, X, or gamma irradiation. Such a treatment indeed allows to amplify IS copy numbers and to stimulate chromosomal engineering. Particular UV treatments are typically of between 0.5 and 400 mJ/cm$^2$, more preferably of between 1 and 200 mJ/cm$^2$, typically between 1 and 100 mJ/cm$^2$, applied for a period of time of about 5" to 5'. A preferred UV treatment is 4 mJ/cm$^2$ for 30 seconds.

During the whole process, the cells may be placed in a suitable culture medium such as, without limitation, PGY (Bacto-peptone 10 g/L, Yeast extract 5 g/L, glucose 20 g/L) or LB (Bacto-tryptone 10 g/L, Yeast extract 2.5 g/L, Sodium chloride 10 g/L). It should be understood that other suitable culture media are known to the skilled person (Buchanan et al., 1974; Difco, 1995) or may be prepared by the skilled person from such known media.

For targeted insertion by homologous recombination into an IS, the gene to be inserted (or amplified) is typically assembled as a recombination cassette, which may be cloned or not in an appropriate vector, such as pMD66. In this regard, the invention shows that linear DNA molecules can be used directly for transformation of *Deinococcus* bacteria. The recombination cassette typically comprises the gene flanked, on one or both sides, by an HR1 region and/or an HR2 region (of about 100-1000, more preferably about 200-700, such as 300-600, typically about 500 bp each), said HR1 and HR2 regions being homologous, respectively, to a 5' and 3' DNA sequence of the targeted IS element. HR1 and HR2 can be any part of the sequence of the target IS. HR1 and/or HR2 allow insertion of the gene of interest into the chromosome by specific homologous recombination. The recombination cassette may comprise, in addition, e.g., a marker gene (such as a drug resistance gene). In such a case, the two genes (gene of interest and marker gene) may be placed under the control of either one promoter (operon structure) or of distinct separate promoters. Examples of marker genes include antibiotic resistance genes such as genes conferring resistance to e.g., kanamycin, chloramphenicol, bleocin, oxytetracycline, hygromycin, erythromycin, puromycin, or thiamphenicol. The recombination cassette (or the vector carrying the same) is introduced into the selected *Deinococcus* strain. Introduction may be performed using techniques such as transformation, lipofection, calcium-mediated precipitation, electroporation, etc. The presence of the recombination cassette or vector in the cell can be verified by e.g., detection of the gene or marker gene. After introduction in the host strain, integration of the recombination cassette in the IS target site(s) occurs by homologous recombination. In this regard, in a preferred embodiment, insertion is induced or stimulated by thermal shock. Indeed, upon thermal shock, the vector is lost and recombinant strains expressing the gene have therefore inserted the gene into their chromosome. The results presented in the examples show effective insertion by IS-targeted homologous recombination. They further show that transformation of *Deinococcus* is effective with a linear DNA construct. They further show that IS-targeted homologous recombination into *Deinococcus* can be performed with very large recombinant cassettes. Indeed, as shown in Example C, a recombinant cassette of more than 6 kb (e.g., comprising 4 distinct genes) can be successfully inserted into a *Deinococcus* bacterium by IS-targeted homologous recombination.

In this regard, the invention also relates to a method for introducing a DNA into a *Deinococcus* bacterium, the method comprising:

providing a linear DNA molecule, and introducing said molecule into a *Deinococcus* bacterium.

More preferably, the linear DNA molecule comprises an HR1 and/or HR2 region as defined above and the method further comprises a step of maintaining the *Deinococcus* under conditions allowing homologous recombination.

In a particular embodiment, the linear DNA molecule comprises more than 2 kb, even more than 3, 4, 5 or even 6 kb.

In an alternative embodiment, IS-mediated insertion is performed by construction of an artificial transposon containing the gene, and introduction of the transposon into the selected *Deinococcus* bacterium, leading to IS-mediated insertion into the chromosome. The artificial transposon preferably comprises the gene, a transposase gene of a *Deinococcus* IS element, optionally a marker gene, and one or two IR elements of a *Deinococcus* IS element. The artificial transposon of the present invention can be constructed using regions or sequences of any IS element as described in Table 1 as starting material. Preferably, the transposase gene and IR sequences are derived from (e.g., have a sequence of a domain of) a same IS element. The transposase gene may be located inside the artificial transposon, that is the transposase gene may be located between the two inverted repeats. Alternatively the transposase gene may be located outside the artificial transposon. In that case, it may be on the transposon-carrying vector, or on the chromosome, or on a distinct vector. The expression of the transposase may be under the control of its own promoter, a constitutive promoter, or an inducible promoter. The marker gene, when present, can be e.g., any gene conferring resistance to an antibiotic such as kanamycin, chloramphenicol, bleocin, oxytetracycline, or hygromycin. The constructed artificial-transposon is typically cloned into a suitable vector, such as pmD66, and introduced into the selected *Deinococcus* host strain. Upon introduction, IS-mediated insertion of the transposon occurs. If desirable, DNA-damaging agents such as gamma and/or X-irradiations and/or UV treatments or, more generally, any treatment allowing or increasing expression or activity of a transposase, may be applied to enhance the transposition and increase integration and amplification of the artificial transposon in the *Deinococcus* host cells. Indeed, it has been shown that irradiation can induce transposition in *Escherichia coli* (Eichenbaum and Livneh, 1998).

Another alternative embodiment for performing IS-mediated multicopy insertion of a gene into the chromosome of a *Deinococcus* bacterium is to use group II introns targeting IS sequences. Mobile group II introns are catalytic RNA elements present in a wide range of prokaryotic and eukaryotic organisms (Michel and Feral, 1995). Some of these introns can mobilize autonomously at a high frequency to allelic sites in a process known as homing. Mobile group II introns possess an intron-encoded protein (IEP) that has reverse transcriptase, RNA splicing ("maturase"), and DNA endonuclease activities (Frazier, Filippo, Lambowitz, and Mills, 2003). Mobility initiates when the IEP helps the intron RNA fold into the catalytically active RNA structure to promote splicing, resulting in ligated exons and an intron lariat-IEP ribonucleoprotein (RNP) complex. The RNP complex recognizes specific DNA target sites and promotes integration by reverse splicing of the intron RNA directly into one strand of the target DNA. The IEP then cleaves the opposite strand and uses it as a primer for target DNA-primed reverse transcription of the inserted intron RNA. The resulting cDNA copy of the intron is integrated into genomic DNA by cellular recombination or repair mechanisms. DNA target site recognition by the RNP complex involves the base pairing of intron sequences denoted EBS1 and -2 (exon binding sites 1 and 2) and δ to sequences denoted IBS1 and -2 (intron binding sites 1 and 2) and δ' in the DNA target site.

The EBS sequences can be mutagenized to retarget the intron to invade a selected IS sequence in *Deinococcus*. In the present invention, a plasmid such as pMD66 carrying the IEP protein (reverse transcriptase)-encoding gene and the group II intron which contains in its sequence a multiple cloning site allowing the cloning of the gene of interest was used. The expression of group II intron harboring the gene of interest is controlled by a constitutive or inducible promoter, such as the T7 constitutive promoter whereas the IEP (reverse transcriptase)-encoding gene is under the control of an inducible or constitutive promoter. Alternatively, the group II introns harboring the gene of interest is integrated into the *Deinococcus* chromosome and the reverse transcriptase encoding-gene carried by a replicative plasmid is under the control of either a constitutive or inducible promoter. This system that uses intron-mediated insertion or amplification does not rely on homologous recombination to achieve multicopy integration and facilitate stable chromosomal gene delivery without selection (Rawsthorne, Turner, and Mills, 2006).

A further object of the invention resides in a method for producing a recombinant *Deinococcus* bacterium comprising one or several copies of a gene of interest inserted into its genome, the method comprising introducing said gene of interest into the genome of said bacterium by IS-mediated insertion and, optionally, amplifying the copy number by subjecting said bacterium or a descendant thereof to a gene amplification treatment.

The invention also relates to a *Deinococcus* bacterium obtained by IS-mediated insertion of a nucleic acid molecule (e.g. DNA fragment), or a descendant of said bacterium.

The invention further relates to a *Deinococcus* bacterium comprising one or several copies of a nucleic acid molecule (e.g. DNA fragment) inserted into an IS element.

A further object of the invention is a nucleic acid molecule (e.g. DNA fragment) comprising a gene of interest flanked, on one or both sides, by a sequence homologous to a sequence of *Deinococcus* IS element, as well as a vector comprising such a nucleic acid.

Still another object of the invention is a nucleic acid molecule (e.g. DNA fragment) comprising a gene of interest flanked, on one or both sides, by a sequence of an inverted repeat sequence of *Deinococcus* IS element, as well as a vector comprising such a nucleic acid molecule.

Chromosomal Engineering

As indicated above, another object of the invention resides in a method for inducing (or increasing) chromosomal engineering (e.g., rearrangement or shuffling) in a *Deinococcus* bacterium, the method comprising expressing in said bacterium a transposase gene. More particularly, the method comprises:

a) causing or inducing expression of at least one transposase in a *Deinococcus* bacterium; and b) selecting a *Deinococcus* bacterium of step a) having a reengineered chromosome.

In step a), the transposase may be expressed on a vector, or chromosome, or supplied as a protein. The transposase is preferably a transposase of an IS element present in said bacterium. Expression of the transposase may be combined with a treatment of the cells to amplify a gene copy number, such as irradiation.

For example a strain expressing one or several transposases can be submitted to an increasing selection pressure (e.g., increasing ethanol concentration to strengthen its resistance to ethanol). A shuffling of the genome will occur due to the expression of the transposases and the most resistant clones will be selected.

The method of the invention may be used to insert any gene of interest into a *Deinococcus* strain, in one or more copies, allowing an increase of its expression. The gene may encode any product of interest, such as an RNA (mRNA, tRNA, siRNA, etc.) or a polypeptide (protein, peptide, etc.). Examples of such polypeptides include, without limitation, enzymes involved in metabolism, any biologically active polypeptide, etc.

The polypeptide may be a polypeptide having pharmaceutical and/or agro-chemical interest. In a particular embodiment, the polypeptide is a pharmaceutical compound (e.g., suitable for use in human or veterinary medicine). Specific examples of such a compound include, without limitation, antibiotics, bacteriostatic compounds, anti-metabolite, chemotherapeutic compounds, antioxidants, anti-inflammatory, polysaccharides, anti-parasitic agents, anti-fungal agents, anti-viral compounds, cytokine-activity compounds, cell-growth factors, hormones, anti-depressives, anti-migraine, anti-asthma, contraceptives, anti-diabetics, psychotropic, anti-arrythmics, enzyme-inhibitors, or adjuvants.

The polypeptide may also have utility e.g., in cosmetics or agriculture, such as pigments, insecticides, pesticides, chemical-degrading compounds, etc.

Examples of enzymes include biomass-degradation enzymes or fermentation enzymes, such as laccases, xylanases, amylases, ADH (alcohol dehydrogenase), PDC (pyruvate decarboxylase), etc. Further examples of polypeptides include enzymes of biological biosynthetic pathways, in particular, enzymes involved in the synthesis of antibiotics.

Further aspects and advantages of the invention will be disclosed in the following Examples section, which is illustrative.

EXAMPLES

A. Characterization of *Deinococcus* IS Sites

A search and compilation of IS sequences present in *Deinococcus* strains was performed by the inventors. A complete list of all identified IS sequences found in different *Deinococcus* species is presented in Table 1 below.

TABLE 1

IS distribution among *Deinococcus* species

| *Deinococcus* sp. | IS200/ IS605 | IS630 | IS701 | IS607 | IS982 | IS3 | IS1 | IS6 | IS5 | IS4 | IS66 | Total of IS | Genome Size (Mb) |
|---|---|---|---|---|---|---|---|---|---|---|---|---|---|
| *D. deserti* VCD115 | 0 | 2 | 1 | 0 | 2 | 5 | 0 | 0 | 1 | 4 | 0 | 15 | 3.86 |
| *D. geothermalis* DSM11300 | 3 | 1 | 17 | 1 | 1 | 0 | 19 | 8 | 12 | 8 | 6 | 76 | 3.25 |
| *D. geothermalis* MX6-1E | 6 | 0 | 6 | 0 | 0 | 0 | 12 | 2 | 1 | 18 | 10 | 55 | 3.25 |
| *D. maricopensis* DSM21211 | 0 | 0 | 0 | 0 | 0 | 0 | 0 | 0 | 1 | 0 | 0 | 1 | 3.5 |
| *D. proteolyticus* MRP | 0 | 0 | 0 | 0 | 2 | 0 | 0 | 0 | 5 | 13 | 0 | 23 | 2.89 |
| *D. radiodurans* | 9 | 10 | 0 | 0 | 0 | 0 | 0 | 0 | 2 | 25 | 1 | 47 | 3.28 |
| Total number of IS among *Deinococcus* sp. | 18 | 13 | 24 | 1 | 5 | 5 | 31 | 10 | 22 | 68 | 17 | 217 | — |

B. Gene Insertion by IS-Mediated Homologous Recombination in *Deinococcus*

Figure 1:
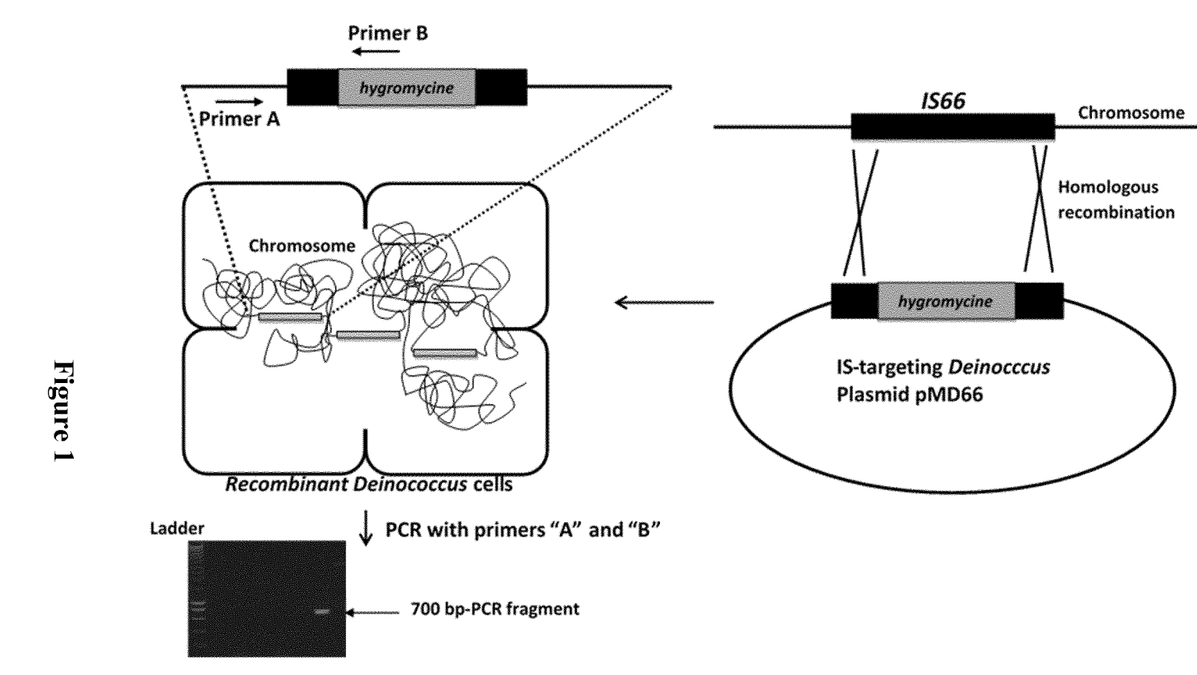
FIG. 1: Gene insertion by IS-mediated homologous recombination in *Deinococcus*.

We built *Deinococcus* plasmids (pMD66-type for replicative, pUC-type for non-replicative) harboring IS-targeting cassettes (see FIG. 1). A DNA fragment containing a gene encoding resistance to hygromycin (grey rectangle) under the control of its own promoter was flanked by two 500 bp regions named HR1 and HR2 (black rectangle), that are homologous to N-term and C-term sequences, respectively, of the insertion sequence IS66 of *Deinococcus* geothermahs. The nucleic acid sequences of HR1 and HR2 are provided as SEQ ID NOs: 11 and 12, respectively. The IS targeting vector is then transformed into *D. geothermalis* and strains expressing the hygromycin gene are selected using the embedded marker on PGY-agar plate containing 800 µg/ml of hygromycin. In an alternative experiment, a linear DNA fragment containing HR1-hygromycin-HR2 was used directly to transform *Deinococcus* cells, the selection of recombinants being carried out as described above. The clones that showed resistance to hygromycin were selected. Such clones are recombinant bacteria having inserted the target nucleic acid into an IS element. In this regard, in order to verify the insertion of the hygromycin resistance-encoding gene into the IS66, the clones were subjected to PCR amplification with primers designated "A" and "B", which anneal specifically to the region upstream the IS66 and to the 5'-end of hygromycin gene, respectively, generating a DNA PCR fragment of about 700 bp (see FIG. 1).

The results presented in FIG. 1 confirm the insertion of the recombinant nucleic acid into the targeted IS.

C. Ethanol Pathway Genes Insertion by IS-Targeted Homologous Recombination in *Deinococcus* Geothermalis An IS-targeting cassette was constructed comprising a PDC gene and two alcohol dehydrogenase encoding genes. The cassette also comprises an antibiotic resistance marker to hygromycin. The cassette is flanked by two 500 bp regions HR1 (SEQ ID NO: 11) and HR2 (SEQ ID NO: 12) (FIG. 2, black rectangle), that are homologous to N-term and C-term sequences of the insertion sequence IS66 of *Deinococcus* geothermalis, respectively. The cassette comprises 6548 bp. The IS-targeting cassette (linear molecule), or a vector containing the cassette, are transformed into *D. geothermalis* and recombinant strains having inserted the cassette into their chromosome are selected using the embedded marker on PGY-agar plate containing 800 µg/ml of hygromycin. The mapping of the cassette in the genome is confirmed by PCR using primers "C" and "D", primer C being specific of each upstream sequence of IS66 and D being specific of 5' end of PDC. The results are presented in FIG. 2. They show the construction has been found integrated into four different loci of IS66 (CDS 1696, CDS 1721, CDS 2881 and CDS 2557 (FIG. 2)), into the chromosome or into native plasmid 1 of *Deinococcus*.

Figure 2:
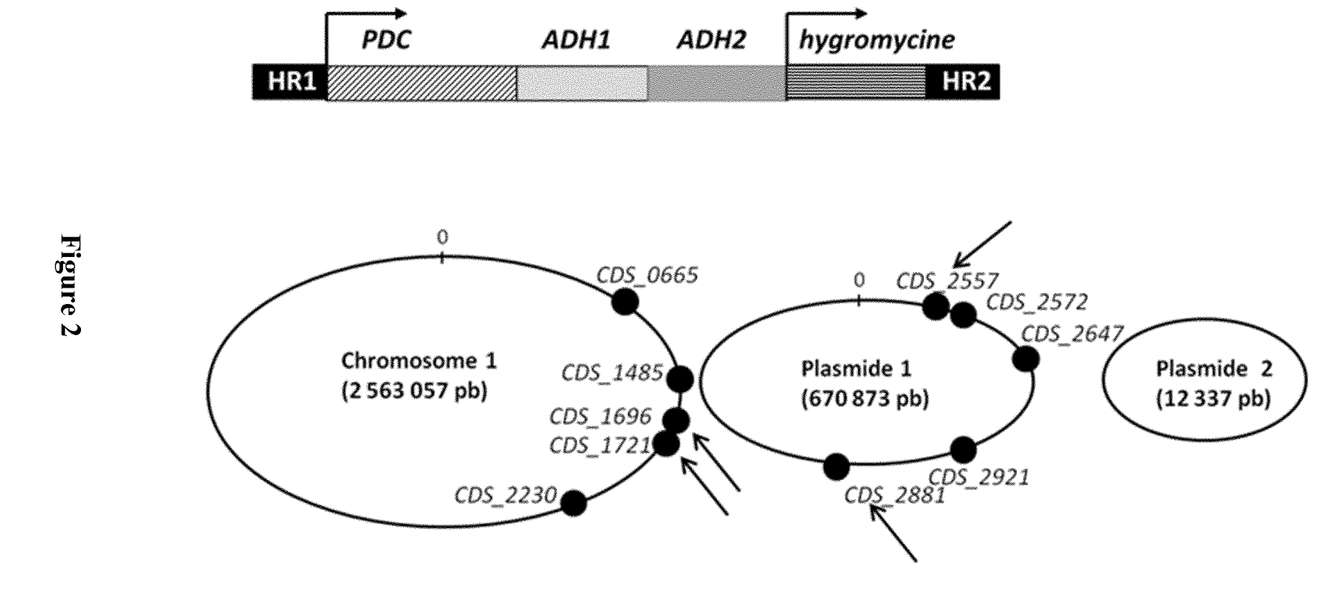
FIG. 2: Insertion of ethanol pathway DNA construct into IS66 of *D. geothermalis*.

These results confirm the efficacy of the method with linear DNA construct. They confirm the specificity of the method since the cassette is found in the targeted IS. They also demonstrate the efficacy of the method with very large expression cassettes.

D. Gene Insertion by IS-Mediated Artificial Transposition in *Deinococcus*

Figure 3:
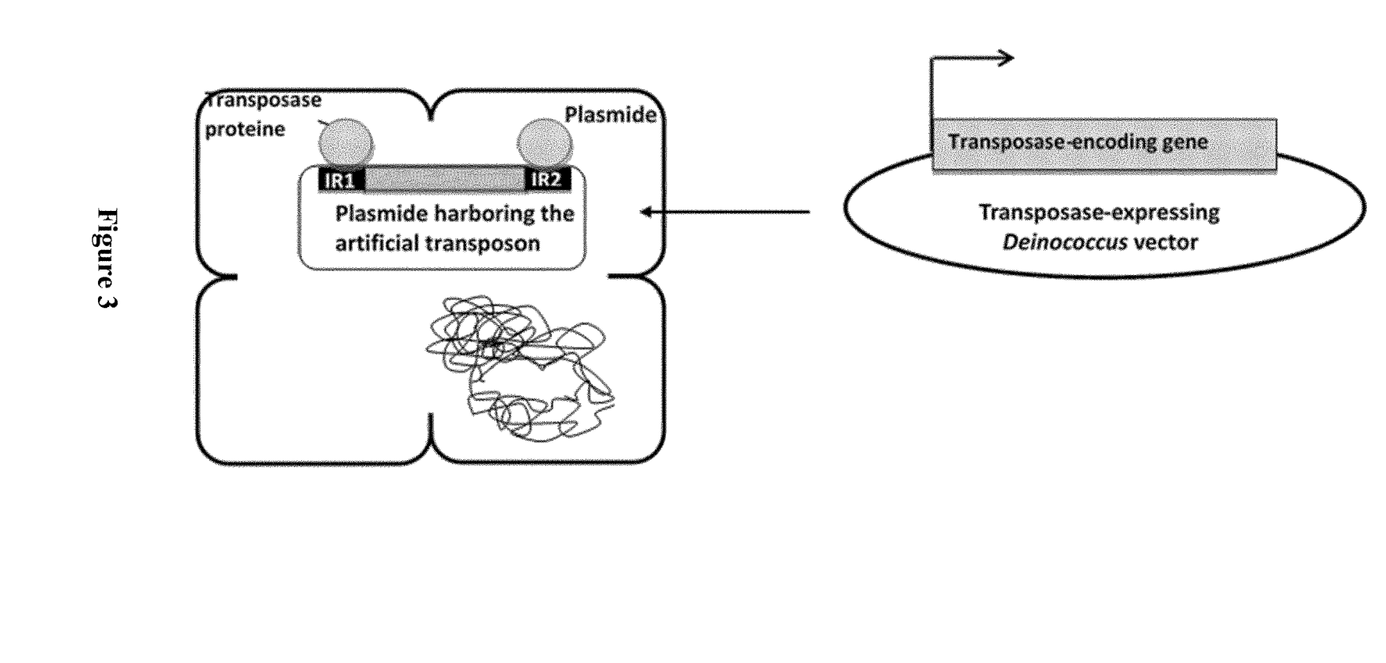
FIG. 3: Gene insertion by IS-mediated artificial transposition in *Deinococcus*.

An IS-propagating cassette is prepared (FIG. 3). The gene of interest is flanked by 2 Inverted repeat sequences (black, IRs) that can be recognized by a Transposase. A *Deinococcus* replicative vector allowing for Transposase thermosensitive-expression is transformed into the GOI IRs strain. Upon Transposase expression (grey), the gene is inserted and propagated into the chromosome.

REFERENCES

Craig, N. L. (1997). Target site selection in transposition. *Annual review of biochemistry*, 66, 437-74. doi:10.1146/annurev.biochem.66.1.437

Eichenbaum, Z., & Livneh, Z. (1998). UV light induces IS10 transposition in *Escherichia coli*. *Genetics*, 149(3), 1173-1181. Retrieved from http://www.pubmedcentral.nih.gov/articlerender.fcgi?artid=1460249&tool=pmcentrez&rendertype=abstract Frazier, C. L., Filippo, J. S., Lambowitz, A. M., & Mills, D. A. (2003). Genetic Manipulation of *Lactococcus lactis* by Using Targeted Group II Introns: Generation of Stable Insertions without Selection Genetic Manipulation of *Lactococcus lactis* by Using Targeted Group II Introns: Generation of Stable Insertions without Selec. doi: 10.1128/AEM.69.2.1121

Gunji et al. (n.d.). U.S. Pat. No. 6,303,381B1.

Islam, S. M., Hua, Y., Ohba, H., Satoh, K., Kikuchi, M., Yanagisawa, T., & Narumi, I. (2003). Characterization and distribution of IS8301 in the radioresistant bacterium *Deinococcus radiodurans*. *Genes genetic systems*, 78(5), 319-327. Retrieved from http://www.ncbi.nlm.nih.gov/pubmed/14676423

Kichenaradja, P., Siguier, P., Pérochon, J., & Chandler, M. (2010). ISbrowser: an extension of ISfinder for visualizing insertion sequences in prokaryotic genomes. *Nucleic acids research*, 38(Database issue), D62-8. doi:10.1093/nar/gkp947

Mahillon, J., Léonard, C., & Chandler, M. (1999). IS elements as constituents of bacterial genomes. *Research in Microbiology*, 150(9-10), 675-687. Retrieved from http://www.ncbi.nlm.nih.gov/pubmed/10673006

Mennecier, S., Servant, P., Coste, G., Bailone, A., & Sommer, S. (2006). Mutagenesis via IS transposition in *Deinococcus radiodurans*. *Molecular Microbiology*, 59(1), 317-325. doi:10.1111/j.1365-2958.2005.04936.x Michel, F., & Feral, J. (1995). STRUCTURE AND ACTIVITIES.

Pasternak, C., Ton-Hoang, B., Coste, G., Bailone, A., Chandler, M., & Sommer, S. (2010). Irradiation-Induced *Deinococcus radiodurans* Genome Fragmentation Triggers Transposition of a Single Resident Insertion Sequence. (Array, Ed.) *PLoS Genetics*, 6(1), 10. doi: 10.1371/journal.pgen.1000799

Rawsthorne, H., Turner, K. N., & Mills, D. a. (2006). Multicopy integration of heterologous genes, using the lactococcal group II intron targeted to bacterial insertion sequences. *Applied and environmental microbiology*, 72(9), 6088-93. doi:10.1128/AEM.02992-05

Robinson, D. G., Lee, M.-C., & Marx, C. J. (2012). OASIS: an automated program for global investigation of bacterial and archaeal insertion sequences. *Nucleic acids research*, 40(22), e174. doi:10.1093/nar/gks778

Sallam, K. I., Tamura, N., Imoto, N., & Tamura, T. (2010). New vector system for random, single-step integration of multiple copies of DNA into the *Rhodococcus* genome. *Applied and environmental microbiology*, 76(8), 2531-9. doi:10.1128/AEM.02131-09

Schneider, D., & Lenski, R. E. (2004). Dynamics of insertion sequence elements during experimental evolution of bacteria. *Research in Microbiology*, 155(5), 319-327. doi: 10.1016/j.resmic.2003.12.008

Tobes, R., & Pareja, E. (2006). Bacterial repetitive extragenic palindromic sequences are DNA targets for Insertion Sequence elements. *BMC genomics*, 7, 62. doi: 10.1186/1471-2164-7-62

The invention claimed is:

1. A method for introducing a nucleic acid molecule into the genome of a *Deinococcus* bacterium comprising introducing in a targeted manner said nucleic acid molecule into an insertion sequence (IS) present in the genome of said bacterium.

2. The method of claim 1, wherein the insertion sequence is present in several copies in the genome of said bacterium.

3. The method of claim 1, wherein the IS is selected from IS200/IS605; IS630; IS701; IS607; IS982; IS3; IS 1; IS6; IS5; IS4; or IS66.

4. The method of claim 1, comprising introducing the nucleic acid into the genome of the bacterium by homologous recombination with an IS present in the genome, by intron-mediated insertion into an IS, or by IS-mediated transposition.

5. The method of claim 1, wherein the nucleic acid comprises a gene of interest flanked, on one or both sides, by an insertion-mediating sequence.

6. The method of claim 5, wherein the insertion-mediating sequence comprises a sequence homologous to a sequence of the IS, allowing IS-mediated insertion of the gene of interest by homologous recombination.

7. The method of claim 5, wherein the insertion-mediating sequence comprises an Inverted Repeat element of an IS, allowing IS-mediated insertion of the gene of interest by transposition or an intron sequence, allowing IS-mediated insertion of the gene of interest by retro-homing.

8. The method of claim 1, wherein the nucleic acid molecule is linear or circular.

9. The method of claim 5, wherein the gene of interest comprises an open reading frame encoding a biologically active polypeptide or RNA.

10. The method of claim 1, wherein before, during, or after IS-mediated insertion of the nucleic acid in the genome of the bacterium, the bacterium is subjected to a gene amplification treatment.

11. A method for producing a recombinant *Deinococcus* bacterium comprising one or several copies of a gene of interest inserted into its genome, comprising introducing in a targeted manner said gene of interest into an IS present in the genome of said bacterium and, optionally, amplifying the copy number by subjecting said bacterium or a descendant thereof to a gene amplification treatment.

12. The method of claim 11, wherein the *Deinococcus* bacterium is selected from *D. deserti; D. geothermalis; D. maricopensis; D. proteolyticus; D. radiodurans; D. murrayi; D. cellulolysiticus; D. guilhemensis; D. aquaticus; D. ficus; D. gobiensis; D. grandis; D. radiopugnans*; or *D. roseus*, or any thermophile *Deinococcus* bacterium.

* * * * *

SEQUENCE LISTING

```
<160> NUMBER OF SEQ ID NOS: 12

<210> SEQ ID NO 1
<211> LENGTH: 1248
<212> TYPE: DNA
<213> ORGANISM: Deinococcus sp.
<220> FEATURE:
<221> NAME/KEY: misc_feature
<223> OTHER INFORMATION: IS3_Deinococcus deserti VCD115-Deide_02801-
      ISDds1

<400> SEQUENCE: 1
tgaggatgac ccgatatggc gtagatggag ataagccctc acgataggag gcaccatcat      60
gactgatcgc agaatccaca ccgccgagtt caagcgagac gcagtgcagc ttgctcgaac     120
gagcggcaac ctgtcgggca ccgcgcgtga cctgggcatc aacagctccc tgctgcgcaa     180
atggatgaat gctgagcagg agaagggcga gttggcattc cctggtcagg gcaaacagct     240
cctcactcca gagcaacagg agatacaacg gcttcgcaag gagaacgaaa tcctgcgaca     300
ggagcgcgag atcctaaaaa aggcggcagc cttcttcgcc aaagaaacca cacgctgagg     360
tatgaattca tccaagatca acgccccgag taccgcctgg acctgctgtg ccgggtgctg     420
gaggtctcgg tgagcgggta ccacagctgg cgaagaaggc cgatctgcga ccgcaaggaa     480
gaggatgcgc tgctcgagca gcgcatccag gaagtgcatc aacgtagtaa acgccgctat     540
ggggcgccac gcattcacgc ggagttgcac gctggaggag tgcgcgtgtc ccgcaagcgg     600
```

| | |
|---|---:|
| gtggcgcgtc tgatgcgtgc cagtggtctg cgggccaagg gaaagcgccg ctgggtgcgg | 660 |
| accacgggga gcagtcacac catggccgtc tgcccgaacc tgcttgagcg gcggttcgag | 720 |
| gtctcgcagc cgaaccaggt ctgggcgttg gacctgacgt atctgcccac gaaagagggc | 780 |
| tggctgtatc tcgcagtcac cttagacctg cattcgcgag ccgtggtggg ttacgcgatg | 840 |
| gacatgcaga tgccagccac cttgccactg gcggcccttc agatggctgc tggccgacgt | 900 |
| cttccgccac caggcctcct tcatcacagc gacaggggca gtcaatacgc gagtggcatc | 960 |
| tttcaggcag aactggcccg catgcgggcc aggggcagta tgagtcgtaa ggggggattgt | 1020 |
| tgggacaacg ccgtggtgga aagcttcttc agctccctga aagggagtt gctgaggac | 1080 |
| accatctttg agacccggga cgtggcccga caagccgtat ttgaattcat cgaggtcttc | 1140 |
| tacaaccgtc agcgtcgtca ctcgtctctt gggtacttga cgcccctgga gttcgaacgc | 1200 |
| caagctacag ctgcttaact tcagctacgc aatatcgggc caggccca | 1248 |

<210> SEQ ID NO 2
<211> LENGTH: 1757
<212> TYPE: DNA
<213> ORGANISM: Deinococcus sp.
<220> FEATURE:
<221> NAME/KEY: misc_feature
<223> OTHER INFORMATION: IS200/IS605_Deinococcus geothermalis DSM11300-Dgeo_2273-ISDge10

<400> SEQUENCE: 2

| | |
|---|---:|
| caaaacgggg tctggggcgg aaaaccaacc ccttcagggg ttggatgcag agtcccagcc | 60 |
| ggccgtcagg gcgggcaggg ctgaggctgt tgcgccgtgt tagtagggggc ttgcgacaaa | 120 |
| cgccgagccg tgtcagtctc tcttcgtggc tgaccagtac aaacacgcca acaccacggt | 180 |
| gtatctgctg aactaccact tcgtgttcat cccgaagcgg cggcggaagg tgctggtcgg | 240 |
| cccggtcgag acgcgcctga aggaagtgct ggcggagaag tgtgcggaga tgaagtggga | 300 |
| cattctcgcc cttgaggtga tgcctgacca cgttcacctg ttccttgccg ccgaccccgc | 360 |
| caccgcgccc aatcaggtga tgcacttgct gaagggctac acgtcgcgga ttctccggca | 420 |
| ggagttcccg cacctgaaca cgctccccgc cctgtggacc cggagctact tcgtgtccac | 480 |
| ggctggggcg gtgagtgggg ccaccatcca aaagtacatc gccgctcaga agacgaggga | 540 |
| ctgaatgacg acgcaccgca aggtctacag gtatcggatt gagccgaccc cggttcaaga | 600 |
| gtcgaagctg tacatgctgg cgggaagtcg gcgcttcgtc ttcaactggg ctcttgcgcg | 660 |
| tcgaagggaa cactacgccg aaacgggcaa gaccctgggg tacaacgctc aggcgggaga | 720 |
| gttgacggcc ctgaagaacc aggaggaaac ctcctggctg aaggaatcgg acagccagct | 780 |
| tctccagcag gccctcaagg acgtggagcg ggccttcgtc aacttctttg agaagcgggc | 840 |
| gaggttcccc cggttcaaga gcaaaaagac ggatactccg cgcttccgta ttccccagcg | 900 |
| ggtgcggata gaggggagcc gtgtgtatgt cccgaaggtg ggatgggtta agctccgcaa | 960 |
| gtctcaggag atagagggca agaccaagag cgcgacgttc aagcgggagg cagacggtca | 1020 |
| ctggtacgtc ttgctcgtct ccgagtttga gatgcccgat gtaccgctgc ccccgtccc | 1080 |
| tgagtccgag gtggtcggga ttgacctcgg cctgaaggat ttctacgtgt tgtccgacgg | 1140 |
| cgggcggaaa gaggccccga ggtttgcccg caaggggcag cggaaactcc gccgcgctgc | 1200 |
| ccgtcgtcac tccaaatgca ccagggggag caaccgcaag gcgaaggcca agcggaagct | 1260 |
| cgcccgtgtt caccgccaga ttgcgaatca gagaaaggac ttcgttcaca aggccaccct | 1320 |
| cggtcttgtt cagcagtacc aggggtttctg catcgagaac ttgagcatca aggggatggc | 1380 |

```
gaaaaccaag ctgtccaaga gcgttctcga cgccgccctg ggagagtttc gccgccagct   1440
cgcctacaag gcccagtggc accggaagtg gctggcggtc atagaccgct ggtttccgtc   1500
cagcaagctg tgtggggaat gcggcagcat caacgcagac ctgaccctga gtgaccggga   1560
atggacgtgc gaatgtggag cggttcacga ccgcgacctc aacgccgccc ggaacatcaa   1620
gcgggaaggg ctttcgcaaa tcgtcgtcgc ggggcacgcg gagacgttaa acgctcgggg   1680
agagggtgtc agacctgcga tagcgggcag ccctcgatga agcgagaatc caacggcttt   1740
agccgttgga gtgtcaa                                                  1757

<210> SEQ ID NO 3
<211> LENGTH: 1071
<212> TYPE: DNA
<213> ORGANISM: Deinococcus sp.
<220> FEATURE:
<221> NAME/KEY: misc_feature
<223> OTHER INFORMATION: IS630_Deinococcus geothermalis DSM11300-
      Dgeo_1042-ISDge7

<400> SEQUENCE: 3
ttattgagtc cggcatgggt tggagacgac aggtacactg agggcgtgct ccgcgtctgg     60
cgaccctcga ccctgacccg cgaccaactg gaggaacggc ggctctatgc tcagcaactc    120
ctagccacag gcgagatcag taccaaggaa atcgcggaaa cgctcggcgt ttccgaaagt    180
accgtccgaa cctggaagca gcgcctccgt gagcatggga gcctcaaggc tacccaagct    240
ccggggcctc cccagcgcct gagtccagaa cagcgtgctc agttggagga actgctccgc    300
gaaggacctc tggccgctgg ctaccccgac tcgcgttgga ctacccctcg cgtgcgggcg    360
atcatcggaa cgcactttga cgtgtggtat cacgccgatc acgtcagaac agtccttcat    420
cagctcggct tcagtcctca gaagccagaa ccgcgtgccc tggaacgcaa tgagcaggcc    480
attcagactt gggtcgagca cacgctcccc gagttggaaa aaaaaggtcg agcagggcgc    540
gaccctcgtc ttcctcgatg aaagtggctt cagtctgaag cccaccgtga cccgaacctg    600 ggccccctcga ggacaaacac cgatccttcg gacgaaagca gcttgggaca agctctcgac   660
catcggggcc atcaccacga gcggccagtt cctgcaacac acacactcgg gagccattcg    720
aggtgctcag gtggtggcct tctgccaaca tcttctccgg cacgtgcagg gtgaattcgt    780
tgtgctgatg gataacgccc gcatccacaa aacgaaggcc ctgagggcct tcgttgagca    840
gcaaccgcgt ctcaccatcg aatatcttcc accttacgcg cctgacctca accccattga    900
gcgggtgtgg gcctacatca aaggaccaat cctgggcaac ttctgcgcca aggacatcgg    960
cgaattgaag gggagactga aggctgcctg gcaacgtgtt cgctacgttc agctccccca   1020
gcgcctcgcc cgcccctacc gtgcgtccca aacctaagcc ggagtcaata g            1071

<210> SEQ ID NO 4
<211> LENGTH: 1150
<212> TYPE: DNA
<213> ORGANISM: Deinococcus sp.
<220> FEATURE:
<221> NAME/KEY: misc_feature
<223> OTHER INFORMATION: IS701_Deinococcus geothermalis DSM11300-
      Dgeo_3008-ISDge5

<400> SEQUENCE: 4
tcaggagttg cacctgaata ggtagcgaag aagcgctccc agacgcgaga atctggggat     60
gtcgaattcg cagattctgg gggagcgcgc ccgtattctg gcagatcagc tcctcgctgt    120
```

```
gcccaccacc gtctatcagc agcgcagctt gcaagctgcg ctgcacctgt tcctcgatac    180
ggggaccaaa accgccctgc accgtgcgcc gctggtcagc aagagtgcgg tgagccgctt    240
gttgaacaat tatgactggg atacagcggc ctgctgggcg ttgctccagc gcagccagtg    300
ggaggccctg ctgctcgccg cacgacgcaa gcgtcgtgcc tgcctccggt tgagcgtgga    360
cctgaccagc atcgagaaga cgggcaagca attgcccttc gtccgcgtct acaacgaagt    420
ccacggcatt catctggtcg tgctgtttgc cgaataccgg gggctgaaat tcccggtggg    480
gtatcgggtc taccggggaa agggcacagc aaccccgtg tcgctcgccc tggaattgct    540
gggggaggtg cccgacgcca ttcggaagcg ctttcgaatc cgtgtgctgg cggacagcgg    600 cttttgaagcc gctgtcttcc tggatggggt tcgtaccctg ggcttcgagt tcgtcgtcgg    660
cgtccgagcg actcggcgta ccacccatcc cggtcaagtg acggtggcgg actgcgaaca    720
tggggcctgg ctggaattgc agaactggcc gcatgacacc ctgaccctcg cccgagttga    780
gcggggagag cggaccttt tctcggtcgc ctcagagttg atgacgggag acgaagtggc    840
cgccgagggg ggcaagcgt ggaacatcga gtccttttc aaggagggca agcaccagtt    900
tagtctccag cagttcgcct tgcgaactgc ccgcggctta gaccgctggg tgctgctggt    960
gtttctcgcc ttcaccttaa cgatgctgca ccgctcgcct gacctctcgc ttgaagaggc   1020
cgcagggctg gccttgaccc tggccctccc tttcctccgc ttgaacgtca tcttcgcccg   1080
cctcgccaca gacgaggaat ttctgcgcca gcacggctat tcactcaaaa ttgcaaggtg   1140
caactcctga                                                         1150
```

<210> SEQ ID NO 5
<211> LENGTH: 907
<212> TYPE: DNA
<213> ORGANISM: Deinococcus sp.
<220> FEATURE:
<221> NAME/KEY: misc_feature
<223> OTHER INFORMATION: IS982_Deinococcus geothermalis DSM11300-
      Dgeo_1090-ISDge8

<400> SEQUENCE: 5

```
accgcgaata ggggttgaca gagcaggggg agaaatggca aagggacggt gctcatgtgc     60
cgtcccgacc tcagtttact ccccatcccg gaggcgctcc agcacctcac ggtctggctc    120
actccgcaga tgcctcccaa gctgatccat ccgcacgaaa aaatcagtga cggcgaactg    180
gtcgctgttg ccctgttgca acgcctctac aaagcgccgt atttcaaggg gtggtggaag    240
ctcaatcact gtccccactt cccctccgag gtgcaggccc gaaccgtttt ggaacgcctg    300
acgcctgtaa tggagcgact tgcaaccgaa gtccaggcac tggacttcgt cgctgtggac    360
tccgaaccgc tcccggtgtg caccttcaaa cgcgcgcccc gctgcaagtt caaagggca    420 cgacacggct tcagtactgc tggcccggtc tatgggttca agctgcatgc ctggaccacc    480
ctgaacggca agatcgctaa gtatgagatc cggcccgcca acgaacacga cttcacggtc    540
gggtgcgtga tgaaccagga ttggcccgcc tatgggagga atggcgtcct caggggcgtc    600
cgttcaagac gaacagggcc gaagcaaatt ggggacaaag gctaccagtc gggcacctat    660
ctgacgcctc ccaagaagaa tgccaagcga tctgaccctc ggtggaaaga gaatatgcg    720 gcagctcgta agatcatcga atcggcgttc tccgtcctgg tcggctccgg gctgcgctgg    780
gggcaggtca aaaccctggt tagtctctgc cttaaggtcg ccctcctcgt cctggcgcac    840
aacctcaagt tccttgacct ctcccccctga tcacagccca gcctccgagt caaccccatt    900
tcgcggt                                                              907
```

<210> SEQ ID NO 6
<211> LENGTH: 748
<212> TYPE: DNA
<213> ORGANISM: Deinococcus sp.
<220> FEATURE:
<221> NAME/KEY: misc_feature
<223> OTHER INFORMATION: IS1_Deinococcus geothermalis DSM11300-
Dgeo_0430-ISDge2

<400> SEQUENCE: 6

```
ggtagtggct gcgacgacgt gatgtaatgg aggggtgccc gagtgcccaa cctgtcagag      60
catccagacg gtcaagaacg gaaaggccaa aacggcacc cagacgtact tgtgtaaggt     120
ctgtggtcgt cgcttccacc ccaacgccag acctgtggcc cacagtgaag cgaccaagga    180
gcagattctc caggcggttc atgagcgaat gagcctcaga ggcgtacagc gcgtgtttgg    240
cgtccaccgc aacaccgtca tccggtggat aaaaaggggg cctccgaagt gaggcagacc    300
gtaccggtct gcctcacacc tcccgaagaa gtggtggttg agctggatga attgtggacc    360
ttcgtgggca agaaaaagca ggcgaggtgg ctctggattg ccctggagcg cagcacccga    420
aaggtgctgg cttgggttct gggcgaccgg agtgagcaaa ccgcgttcaa gctctgggac    480
cgcttgccgc tgtccccaga acagcgcctg aagggcacgt tttgcacgga cctgtggcgt    540
gcttacgacg agccactcct gggggtgaag cggctcaccc gcaaggggga aacgaaccac    600
gtcgaacggc tcaactgcac cctcagacag cggctaggtc ggctggtccg caagtcgttg    660
tccttctcaa gtccgacga gatgctcgaa gcgagcctga ccctcgcctt ccatcgctac    720
aacctgtcac gttgatgcag ccactacc                                       748
```

<210> SEQ ID NO 7
<211> LENGTH: 806
<212> TYPE: DNA
<213> ORGANISM: Deinococcus sp.
<220> FEATURE:
<221> NAME/KEY: misc_feature
<223> OTHER INFORMATION: IS6_Deinococcus geothermalis DSM11300-Dgeo_
2913-ISDge13

<400> SEQUENCE: 7

```
ggttctgtca ggttaagttc gggtaggctg gtttatcgtg cctgctgacc cgaagcccta     60
tcgccaccgt ttccccaaga gcatcatcca acacgccgtt tggctgtatc accgcttccc    120
tctcagctac cgagatgttg aagaattgct gctccaacgc ggaattcaag tcagtcacga    180
aacaattcgt gactggtgcg ataagttcgg ccccaccatc accaaggaat tgaagaaacg    240
ggaaccccat cggggttccc attggcacct ggatgaagtc tgcgtcaaga tcaagggcgt    300
caagcactgg ttgtggcgtg ccgtggacga gcatggcgct gtgctggatg ttcttctgca    360
agaacaccgc gacactgagg cggccaagat gttcttcact atgttgctga gcaactacga    420
ggctccaacc accatccaca ccgacaaact gggcagttac agagcagcca ttcgtgagat    480
tcctgaactt catggtgcgc tgcaccgtga agtgatttcg acggccaggt gcaacaattt    540
gattgaacag tcgcaccgac cgacacgaaa tcaggaacga agccagaaag gcttcaaggg    600
catagagaac acacagaaat tccttgatct acacgccaga accagcaatc tccaccagtt    660
cacgcgaacg accgtgaccg ccaaaacgag acgaagcaac cagagaaccg cttttcaaac    720
ctggaacgag gttgcgctgc tcgcagcctg accaatcagg ccaccctgcc cccgtcaacg    780
tcgcaaaaac ttaacctgac agaacc                                         806
```

<210> SEQ ID NO 8
<211> LENGTH: 1117
<212> TYPE: DNA
<213> ORGANISM: Deinococcus sp.
<220> FEATURE:
<221> NAME/KEY: misc_feature
<223> OTHER INFORMATION: IS5_Deinococcus geothermalis DSM11300-
      Dgeo_2191-ISDge6

<400> SEQUENCE: 8

| | | |
|---|---|---|
| agacccgctg cgaaataggg gcggtgtgaa gtagattcgg ggggtgttgc gcgtccagac | 60 |
| gctgaaacgc cggtcccgtg ccttcgaacg cctcatcggt ctgactcctg agcagttcga | 120 |
| cgctttgctg gccgacctcg aaccggagtg ggagcgcgct cgtcgtcgct ccctgctgcg | 180 |
| tgctgaccgc gttcgggcga ttggcggtgg ccgcacccac aagctggaac tgccagagcg | 240 |
| cctcttggtg acgttgctct atctacgtca gtacttcacc gtccacgtcc tcgggatgtt | 300 |
| cttcgacctg gacgacagca acgtgtgccg caacattcac gccctgctgc ccgtcctgga | 360 |
| gcaggttctt cccgctcccg tgcgcgccag gacgttggcg ccacgggag acgagccgcc | 420 |
| gaagaagggc gagaagaagc cacgcaagat ccgctcgctc gacgagttcg ttgaagcctt | 480 |
| cccccgagtac gaggacctga tcgtggacgc gaccgagcag cctcgcggcc agcccaaagt | 540 |
| caagaagggt gagacgccgg gcaagaaggc ggtcggacgt ccgaaagaca agaagaagtt | 600 |
| tttcagcgtc aaggcgggca cccatacct caagacccaa gtcgccgtca cgccggacgg | 660 |
| gctgattcgg cacctgagcg ccccgtgcc gggccggatg cacgacatgc gcctcttgcg | 720 |
| ccgctcccgg ctggaagggc gcgtgccgcg ccacgtgcgg ctgtggggcg atcggggcta | 780 |
| caccggactc gacacgctct acccggaccg agagacggtg gtgccccgca agaagcccaa | 840 |
| gaaaggcgtg ctcagcgacg aagacaagga gatgaaccgc ctgatcgcca aggtgcgcat | 900 |
| cacggtggag aacgtcctgt gtcagatcaa gaagtaccgg gcgtgtggag agttcttccg | 960 |
| caatcccatg aagcggcacg gggtgatgtg gggatgcgtg gcaggcctgg tgaacctacg | 1020 |
| aacgctcgac cgcttggccc tccatcccgc ctgaacgacc cagcaacgac ggagagccgt | 1080 |
| gcctggtcgg cacggccct tgtttcgcag caggtct | 1117 |

<210> SEQ ID NO 9
<211> LENGTH: 1127
<212> TYPE: DNA
<213> ORGANISM: Deinococcus sp.
<220> FEATURE:
<221> NAME/KEY: misc_feature
<223> OTHER INFORMATION: IS4_Deinococcus geothermalis DSM11300-
      Dgeo_1784-ISDge9

<400> SEQUENCE: 9

| | | |
|---|---|---|
| ctctctaggg gtcaaaactc agatggagac ttgagaagtc ggctcctgta cggtgttttc | 60 |
| tgcgatgaaa gacacccgga gccgacccgc tcagtctagc ctcactgccc tgcttgctga | 120 |
| gcacttcccg ctggatcctc gtcgcctgac cgtcttgagc gccctgatct tggccgtgat | 180 |
| tcaggcacga agcgtcgttc tttaccagct cgtccagatc gttgaccttc ccggctcaaa | 240 |
| cgacaccgtg taccaacgcc tgaagcgctt cgtgcaattc gcacttcctg atctcctggt | 300 |
| tgcccgcttc gtcctggccc atctgcgaga cgagcagcat ctgctgctcg tcctggaccg | 360 |
| caccaattgg aagctcggtc agcaggacat caatattctc ctgctcagtg tgcggtggca | 420 |
| gaccttcagt ttcccgctcg tctggacctt gttgccgcat agcggcaaca gcaacatggc | 480 |
| gacccgcatc gcgctggtcg aacgcctgct cccattgctc cagggcaaga cactcttcct | 540 |

```
ggccgctgac cgagagttcg tcggtgggga gtggttcgtg gccttgcgcc gcatgagcct      600
ttctcccgtg atccgtttgc gggctgacag catggtcgag gggtcccag  tctgggtcag     660 attcaagaaa ctcaagccgg gtgaagtgcg ggtctggtac aagcccactc acgtctacgg      720
cgtgacgctg cgcgttctag cgtgccagaa cgtccacggc cagactctct tcctggctta     780
ccaaggccat gctgaaaaag ccctgaaacg ttacgcgctg cgctggacag cagaaaacat     840
gcatcaggcg ctgaaatcca ggggcttttt tctcgaaagc actcacctga ctgatcccag      900
tcgggtttcc acgctcctgg ccgtggtcgc actggccttt gtatggtgct gtttagtggg      960
agagtttgag cagcagcgtg acccgtcacg ctgcctcagg cacggctatc cccccaaaag     1020
cctcttcaga cgtggcctgg atgcccttcg cgccgtgctg accaagccca accgtggggc     1080
tgcacgcgcg tttcccgact ttctcgccac ttttgacccc tagagag                   1127
```

<210> SEQ ID NO 10
<211> LENGTH: 1453
<212> TYPE: DNA
<213> ORGANISM: Deinococcus sp.
<220> FEATURE:
<221> NAME/KEY: misc_feature
<223> OTHER INFORMATION: IS66_Deinococcus geothermalis DSM11300-
      Dgeo_0266-ISDge4

<400> SEQUENCE: 10

```
gtgactactc agcagggga gttgatgtct gcggcaaggt agagtagggc atcacacagg       60
acgcctgccc gaactgccaa cgactggaag ctgaacttgt gcagcttcgt caggaacttg      120
agcgtctgaa ggcagagcta cgcgaactga atcccgtct gaaacgcgat agtgagactt      180
caaatcagcc accgagcaaa gacccgccct ggaagcccaa agtgagcgg cagaagagcg      240 aacgctcttc tggtggtcag cgtggtcatc cggggaaaac cctgaaattc agtgacgaac      300
ccgatgacat ccagcccctc ccgctcacgg gtcaatgcgg gtgtggacaa gcgtgggacg      360
aggtgaaggc gactgaacat ctggcccggc aggttcacga cctgccggaa ctgcgcctgc      420
acatcactga atttcaggct gaagtcaaaa tctgtcccag gtgtggttgc cggggacagg      480
cggcttttcc tgagcatgtt cctggacagg tgcaatacgg gccgcgcctg cacgccctga      540
cgacatattt gaatgtggtg catttcgtac cactgcaacg ggtaactcag atcacggacg      600 cgcttttttgg cgcgtccatc agcgatggca ccgtggctct gaacatcaat ctggcctcag      660
agcgcctcaa accgtttgag gacgacctga aggctggact caggcagcaa cccgtgctgc     720
acgcagatga aacgggcgca aaggtgaatg gcaaattgaa ctggttccat gtcgcgtgct     780
ttgctggtgg gacgctctac acgctgcatc cgcaacgagg ctatgccgcg atcaaagccg      840
ccggtgtcct gtctgacttt ggggcgtcg tggttcacga cgcttggaac acctatttcc       900
gtctgccagg ggaacatgcg ctgtgcaatg ctcacctgtt gcgggagtta cgcaaactgg      960
atgagcatga cgggcaaccc tgggccggtg aactgcgacg cgaactccag caggtctacc     1020
acttgcaaaa atcaggagga atcaccgaac agcagaaaat ggccttctat acacgctttg     1080
acgaactggt gcaggctgct ctggaagcca cccagtgca ggaacccatt ccaaaacagc     1140
gtggaaaacc caaacaactt ccagggagga acctagcctt gcggtgccag cagcatcgcg     1200
ccgcgatgct gcgctttctg aacgtgatg atgtgcccttt tgataacaac caggccgagc     1260
gtgacatcag gatgctatgc gtgaaacgca aggtttcagg tggttccgc tctgaggcgg     1320 gtggcgaggc gttctgtcgc attcggagtt tcgtgtcaac ccttcacaag cagggtctat     1380
```

```
ccgtttggga cggtttagtg gatgttttc gcggtgtcct acccaaactc gatttctcgt    1440
gctgagcagt tac                                                      1453

<210> SEQ ID NO 11
<211> LENGTH: 501
<212> TYPE: DNA
<213> ORGANISM: Artificial
<220> FEATURE:
<223> OTHER INFORMATION: HR1 region

<400> SEQUENCE: 11
gtgactactc agcagggga gttgatgtct gcggcaaggt agagtagggc atcacacagg      60
acgcctgccc gaactgccaa cgactggaag ctgaacttgt gcagcttcgt caggaacttg    120
agcgtctgaa ggcagagcta cgcgaactga aatcccgtct gaaacgcgat agtgagactt    180
caaatcagcc accgagcaaa gacccgccct ggaagcccaa aagtgagcgg cagaagagcg    240
aacgctcttc tggtggtcag cgtggtcatc cggggaaaac cctgaaattc agtgacgaac    300
ccgatgacat ccagccctc ccgctcacgg gtcaatgcgg gtgtggacaa gcgtgggacg    360
aggtgaaggc gactgaacat ctggcccggc aggttcacga cctgccggaa ctgcgcctgc    420
acatcactga atttcaggct gaagtcaaaa tctgtcccag gtgtggttgc cggggacagg    480
cggcttttcc tgagcatgtt c                                             501

<210> SEQ ID NO 12
<211> LENGTH: 505
<212> TYPE: DNA
<213> ORGANISM: Artificial
<220> FEATURE:
<223> OTHER INFORMATION: HR2 region

<400> SEQUENCE: 12
ctggacaggt gcaatacggg ccgcgcctgc acgccctgac gacatatttg aatgtggtgc     60
atttcgtacc actgcaacgg gtaactcaga tcacggacgc gcttttggc gcgtccatca    120 gcgatggcac cgtggctctg aacatcaatc tggcctcaga gcgcctcaaa ccgtttgagg    180
acgacctgaa ggctggactc aggcagcaac ccgtgctgca cgcagatgaa acgggcgcaa    240
aggtgaatgg caaattgaac tggttccatg tcgcgtgctt tgctggtggg acgctctaca    300
cgctgcatcc gcaacgaggc tatgccgcga tcaaagccgc cggtgtcctg tctgactttg    360
ggggcgtcgt ggttcacgac gcttggaaca cctatttccg tctgccaggg gaacatgcgc    420
tgtgcaatgc tcacctgttg cgggagttac gcaaactgga tgagcatgac gggcaaccct    480
gggccggtga actgcgacgc gaact                                         505
```

UNITED STATES PATENT AND TRADEMARK OFFICE
CERTIFICATE OF CORRECTION

PATENT NO. : 10,358,657 B2
APPLICATION NO. : 15/039867
DATED : July 23, 2019
INVENTOR(S) : Rémi Bernard et al.

It is certified that error appears in the above-identified patent and that said Letters Patent is hereby corrected as shown below:

In the Specification

Column 9,
Line 57, "geothermahs." should read --*geothermalis*.--.

Column 10,
Line 12, "Geothermalis" should read --*geothermalis*--.
Line 21, "geothermalis," should read --*geothermalis*,--.

Signed and Sealed this
Sixteenth Day of June, 2020

Andrei Iancu
*Director of the United States Patent and Trademark Office*